April 25, 1972 R. E. PETERMAN Plant Pat. 3,142
WALNUT TREE
Filed Dec. 29, 1969
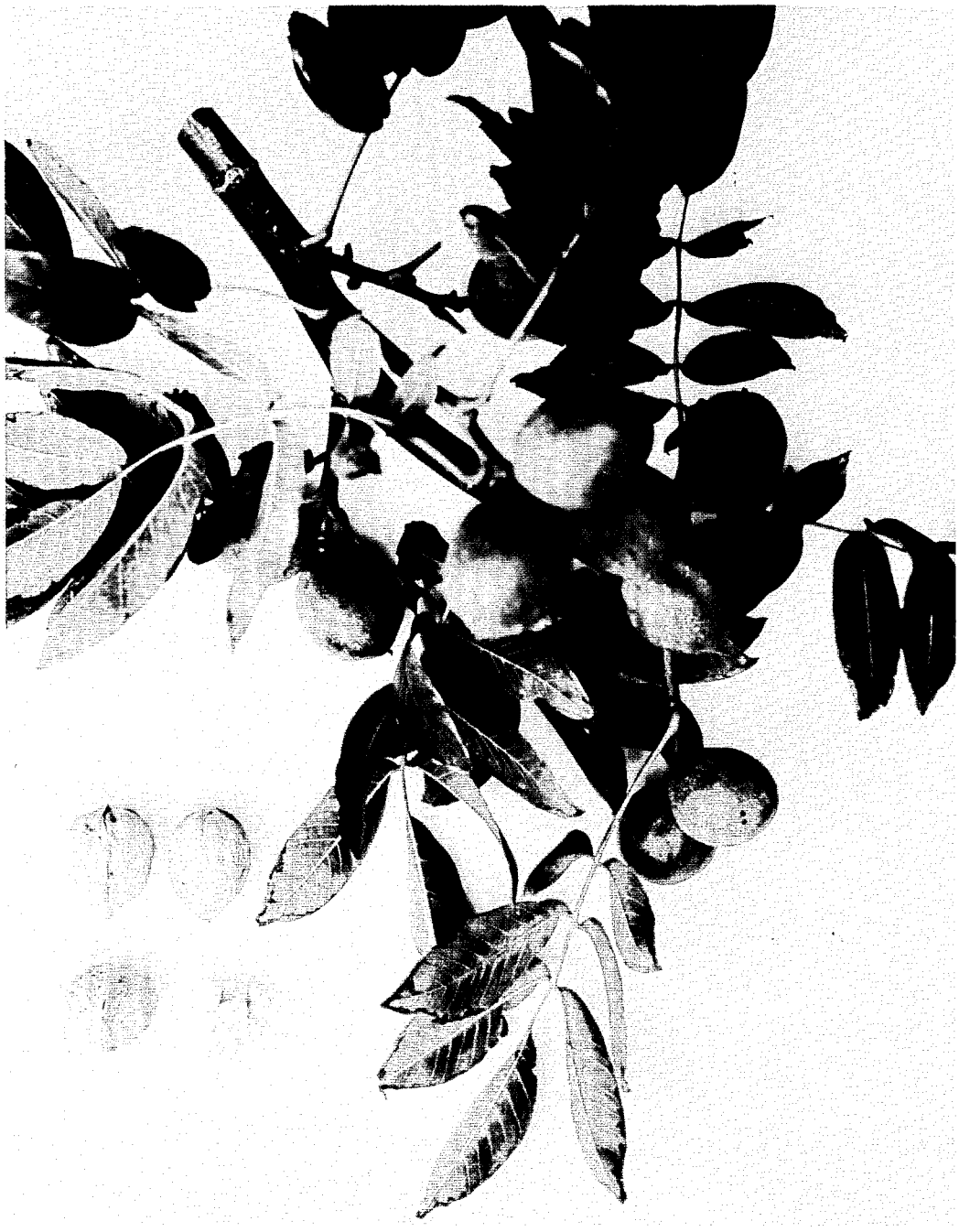
INVENTOR
Rodney E. Peterman
BY
Webster & Webster
ATTORNEYS

United States Patent Office

Plant Pat. 3,142
Patented Apr. 25, 1972

3,142
WALNUT TREE

Rodney E. Peterman, 2606 W. Linne Road,
Tracy, Calif. 95376

Filed Dec. 29, 1969, Ser. No. 889,008
Int. Cl. A01h *5/03*
U.S. Cl. Plt.—32 1 Claim

ABSTRACT OF THE DISCLOSURE

A new and distinct variety of English walnut tree, of general adaptability, which is vigorous in growth, of medium size in maturity, of medium form, of medium density with large leaves, the time of leafing being very early, and a regular and very productive bearer of large nuts; the nuts—which are very early in forming and relatively early in ripening—are of good quality and have crisp kernels of excellent flavor.

ORIGIN OF THE VARIETY

The present variety of walnut tree was discovered by me growing among a planting of several hundred trees, of the Payne (unpatented), in an orchard on my ranch located near Tracy, San Joaquin County, California. Subsequent to my discovery of the original tree of the present variety, and which discovery was occasioned by my recognition of certain distinctive characteristics in comparison to adjacent trees of the Payne, I maintained such original tree under close and careful observation in order to confirm its novelty and to determine its potential for commercial growing.

ASEXUAL REPRODUCTION OF THE VARIETY

The present variety of walnut tree was asexually reproduced by me on my ranch, located as aforesaid, by budding from the original tree onto California black walnut seedlings. In maturity, all of such asexual reproductions ran true to the original tree in all respects.

SUMMARY OF THE VARIETY

The present variety of walnut tree is distinctively characterized by vigorous growth, medium size and form in maturity, medium density with large leaves, the time of leafing being very early, and regular and very productive (as good or better than Ashley, United States Plant Pat. No. 2,168) bearing of large nuts which are very early in forming and relatively early in ripening, of good quality (comparable to Hartley, unpatented), and with crisp kernels having excellent flavor.

The present variety of walnut tree is further distinctively characterized by a flowering habit which includes an extended period (from very early to late season) of pollen shedding, and hence with a substantial and desirable overlap of pistillate blooming. Such extended period of pollen shedding spans forty days or more; the pistillate flowers being similar to the Payne but opening eight to ten days earlier, and five to seven days earlier than the staminate flowers.

The present variety of walnut tree is additionally distinctively characterized by its ability to serve as an effective pollinator for other varieties of walnuts, especially the Payne.

The present variety of walnut tree is still further distinctively characterized by the bearing of nuts which normally are not subject to kernel shrivel; by kernels which average seventy percent light color and thirty percent amber color; and by kernels which have minimal veining or speckling, and none black.

BRIEF DESCRIPTION OF THE DRAWING

The drawing is an illustration, by photographic reproduction in color, of a twig with leaves and nuts; the illustration also including a number of hulled nuts, and a shelled kernel.

DESCRIPTION OF THE VARIETY

The botanical details of this new and distinct variety of walnut tree—with color definitions (except those in common color terms) referenced to Maerz and Paul Dictionary of Color—are as follows:

Tree:

*Parentage.*—Unknown.
*Size at maturity.*—Medium.
*Vigor.*—Vigorous.
*Form of growth.*—Medium.
*Color of bark.*—Medium.

Trunk:

*Form.*—Medium.
*Color.*—Gray.

Branches:

*Form.*—Medium.
*Lenticels.*—Circular; white.
*Branching habit.*—Medium.
*Color.*—Gray, with green fruiting twigs.

Foliage: Density.—Medium.

Leaves:

*Size.*—Large; average length of leaflets—4¾"; average width of leaflets—1⅞".
*Margin.*—Smooth.
*Petiole.*—Similar to Payne.
*Glands.*—Pubescent, not pronounced.
*Time of leafing.*—Very early.
*Color.*—Top side—medium green (23–L–10); underside—Lighter green (22–L–6).

Flowering habit:

*Age at which tree starts producing catkins.*—Very early.
*Number of catkins produced.*—Abundant.
*Size of catkins.*—Large.
*Time of pollen shedding.*—Very early to late season, spanning at least 40 days.
*Age at which tree starts producing pistillate flowers.*—Very early.
*Number of pistillate flowers produced by young trees.*—Very abundant.
*Number of pistillate flowers produced by mature trees.*—Very abundant.
*Number of pistillate flowers per inflorescence.*—Very abundant.
*Time when pistillate flowers are receptive.*—Very early.
*Coincidence of staminate and pistillate bloom.*—Considerable overlap of pistillate bloom.

Crop:

*Bearing.*—Regular bearer.

*Productivity.*—Very heavy.

*Ripening period.*—Early—Sept. 22, 1969. About 7 to 10 days later than Payne.

*Evenness of maturity.*—Medium.

*Quality.*—Good.

*Distribution of nuts on tree.*—Well distributed; many in clusters.

*Tenacity.*—Similar to Payne.

Hull:

*Form.*—Similar to Payne.

*Color.*—Medium green (21–K–9), with many yellow speckles.

Nut:

*Size.*—Large; average length—41.4 mm.; average diameter in suture plane—34.9 mm.; average diameter cheek to cheek—36.5 mm.

*Form.*—Oval.

*Basal end.*—Rounded.

*Blossom end.*—Beaked.

*Weight.*—Average weight (in grams) of ten nuts—139.7; average weight (in grams) of ten kernels—62.4; average percentage kernel to nut—43.5.

*Uniformity of size.*—Average.

*Thickness of shell.*—Medium.

*Seal of shell.*—Good.

*Roughness of shell.*—Medium.

*Fill.*—Moderately good.

*Color.*—Light beige (13–E–6).

Kernel:

*Plumpness.*—Medium.

*Shrivel.*—None.

*Speckling.*—Very few.

*Veining.*—Very few.

*Flavor.*—Excellent.

*Color.*—Yellow (11–K–4) with a light tan tone.

Resistance to insects: No unusual susceptibilities noted.

The walnut tree and its nuts herein described may vary in slight detail due to climatic and soil conditions under which the variety may be grown; the present description being of the variety as grown in the Central Valley of California.

I claim:

1. A new and distinct variety of English walnut tree, substantilaly as illustrated and described, characterized by vigorous growth, medium size and form in maturity, medium density with large leaves, a very early time of leafing pistillate flowers similar to the Payne but opening eight to ten days earlier and five to seven days earlier than the staminate flowers, an extended period of pollen shedding which spans forty days or more, and a regular and very productive bearing of large nuts which are very early in forming and relatively early in ripening, of good quality, and with crisp kernels having an excellent flavor, the kernels averaging seventy percent light in color, normally not subject to shrivel, and with minimal veining and speckling.

No references cited.

ROBERT E. BAGWILL, Primary Examiner